United States Patent [19]

Ide et al.

[11] Patent Number: 4,604,472

[45] Date of Patent: Aug. 5, 1986

[54] OCTAHYDRONAPHTHALENE DERIVATIVES AND THEIR PREPARATION

[75] Inventors: Junya Ide; Shigeki Muramatsu; Yoshio Tsujita; Masao Kuroda, all of Hiromachi, Japan

[73] Assignee: Sankyo Company Limited, Tokyo, Japan

[21] Appl. No.: 753,254

[22] Filed: Jul. 9, 1985

Related U.S. Application Data

[63] Continuation of Ser. No. 421,395, Sep. 22, 1982, abandoned.

[30] Foreign Application Priority Data

Sep. 25, 1981 [JP] Japan .................. 56-151871

[51] Int. Cl.$^4$ ........................... C07D 309/30
[52] U.S. Cl. .................. 549/292; 514/824; 562/501; 560/119
[58] Field of Search ......................... 549/292

[56] References Cited

U.S. PATENT DOCUMENTS

| | | | |
|---|---|---|---|
| 4,246,277 | 1/1981 | Bessin .................. | 514/471 |
| 4,323,648 | 4/1982 | Tanzawa et al. .................. | 549/292 |
| 4,361,515 | 11/1982 | Terahara et al. .................. | 549/292 |
| 4,503,072 | 3/1985 | Hoffman et al. .................. | 549/292 |
| 4,517,373 | 5/1985 | Terahara et al. .................. | 549/292 |

FOREIGN PATENT DOCUMENTS 0076601  4/1983  European Pat. Off. ............ 549/292

OTHER PUBLICATIONS

J. F. W. McOmie, Protective Groups in Organic Chemistry (1973), pp. 341–342.
Chemical Abstracts 93: 45280c.
B. Unterhalt, Pharmazeutische Zeitung, vol. 125(7) (1980), pp. 361–367..

*Primary Examiner*—Glennon H. Hollrah
*Assistant Examiner*—Dara Dinner
*Attorney, Agent, or Firm*—Frishauf, Holtz, Goodman & Woodward

[57] ABSTRACT

Compounds of formula (I):

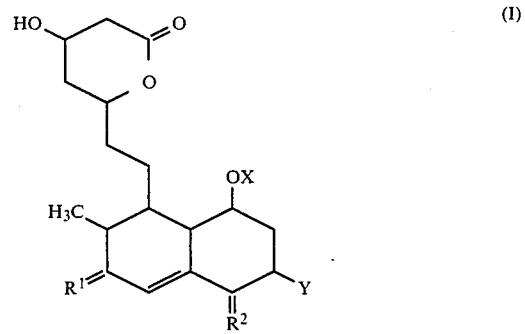

[wherein X represents a hydrogen atom or a 2-methylbutyryl group, Y represents a hydrogen atom or a methyl group and $R^1$ and $R^2$ are the same or different and each represents an oxygen atom or a group of formula $=N—OR^3$ (wherein $R^3$ represents a hydrogen atom or an alkyl group)], the free hydroxy-carboxylic acids corresponding thereto and salts and esters of said acids may be prepared by oxidizing and, if necessary, oximating a corresponding ML-236A, ML-236B, MB-530A or MB-530B compound, and these compounds have valuable antihypercholesteraemic activity.

31 Claims, No Drawings

OCTAHYDRONAPHTHALENE DERIVATIVES AND THEIR PREPARATION

This is a continuation, of application Ser. No. 421,395 filed Sept. 22, 1982, now abandoned.

BACKGROUND TO THE DISCLOSURE

The present invention relates to a series of new octahydronaphthalene derivates, which are derivatives of the known compounds designated as ML-236A, ML-236B, MB-530A and MB-530B, and to a process for preparing these compounds.

In recent years, a number of compounds having the essential skeletal structure of 3,5-dihydroxy-5-[2-(1-polyhydronaphthyl)ethyl]pentanoic acid have been discovered. The first of these, which were designated ML-236A and ML-236B, have the following formulae (i) and (ii), respectively:

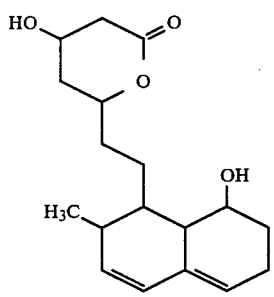

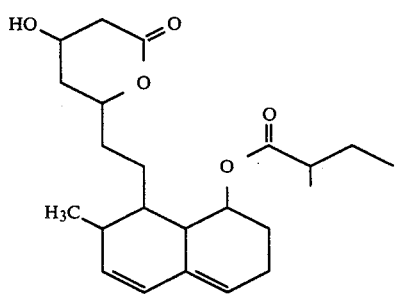

and are disClosed in U.S. Pat. No.3,983,140. These compounds can exist either in the form of a lactone (shown in the formulae above) or as a corresponding free hydroxy-carboxylic acid. They have been isolated and purified from the metabolic products of microorganisms of the genus Penicillium, especially *Penicillium citrinum*, a species of blue mould. They have been shown to inhibit the biosynthesis of cholesterol by enzymes or cultured cells separated from experimental animals by competing with the rate-limiting enzyme active in the biosynthesis of cholesterol, namely 3-hydroxy-3-methylglutaryl-coenzyme A reductase and, as a result, significantly reduce serum chloresterol levels of animals [Journal of Antibiotics, 29, 1346 (1976)].

Subsequently, another compound having a similar structure was discovered in the metabolic products of a mould of the genus Monascus, especially *Monascus ruber*, and this compound, which is disclosed inter alia, in U.K. patent specification No. 2,046,737 may be represented by the formula (iii):

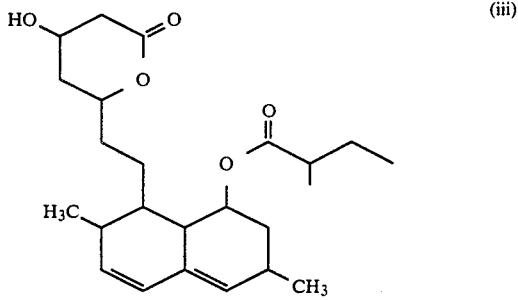

This compound is referred to as "Monacolin K" in that United Kingdom patent specification, but has subsequently been, and hereinafter is, referred to as "MB-530B".

Subsequently, a similar compound, having similar antihypercholesteraemic activity, was disclosed in United Kingdom patent specification No. 2,073,193 and was given the name "MB-530A"; this compound may be represented by the formula (iv):

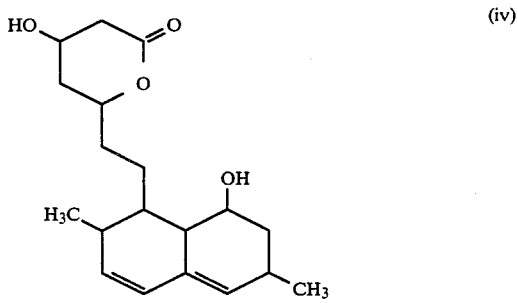

The structure common to all of these compounds is shown below as formula (v), which also shows the numbering system employed herein to identify points of attachment and/or substitution:

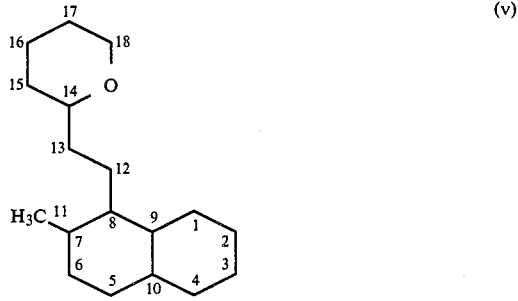

Of the compounds of formulae (i) to (iv), those having a hydrogen atom at the 3 position are called "ML-236 compounds", whilst those having a methyl group at the 3-position are called "MB-530 compounds". The compounds in which the group at the 1-position is a hydroxy group have the suffix "A" (i.e. ML-236A and MB-530A), whilst those having a 2-methylbutyryloxy group at the 1-position have the suffix "B" (i.e. ML-236B and MB-530B).

The free hydroxy-carboxylic acids corresponding to the compounds of formulae (i) to (iv) are named ML-236A carboxylic acid, ML-236B carboxylic acid, MB- 530B carboxylic acid and MB-530A carboxylic acid, respectively.

All of the above-mentioned compounds have double bonds between the 4- and 10- positions and the 5- and 6- positions. The hypothetical compounds having the same structure except that the double bonds are between the 3- and 4- positions and the 10- and 5- positions are named by adding the prefix "Iso" before the name of the parent compound. Thus, the "iso" compounds corresponding to the compounds of the formulae (i) to (iv) may be represented by the following formulae (vi) to (ix):

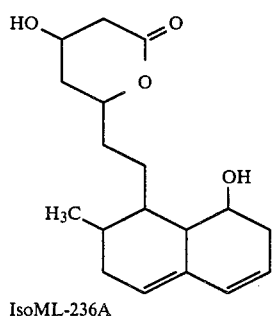

IsoML-236A (vi)

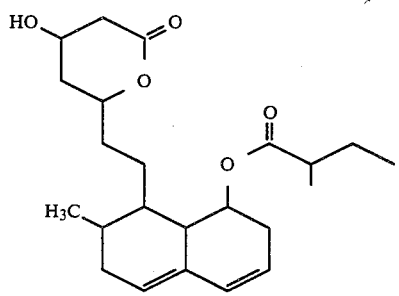

IsoML-236B (vii)

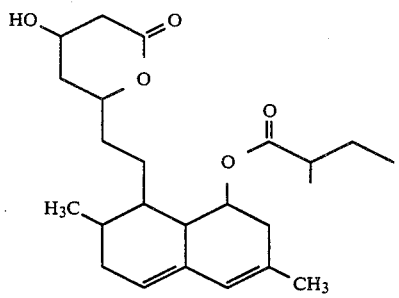

IsoMB-530B (viii)

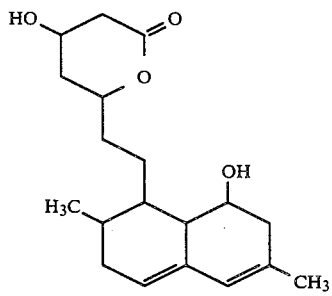

IsoMB-530A (ix)

As will be explained in more detail hereinafter, the nomenclature of the compounds of the invention is based upon the names assigned to the compounds having the aforementioned formulae (i) to (iv) and (vi) to (ix).

BRIEF SUMMARY OF INVENTION

We have now discovered a series of compounds which are derivatives of the ML-236 and MB-530 compounds; many of the compounds have valuable antihypercholesteraemic activity, the activities of some of these compounds being at least an order of magnitude greater than the activities of the known compounds.

Thus, the present invention consists in compounds of formula (I):

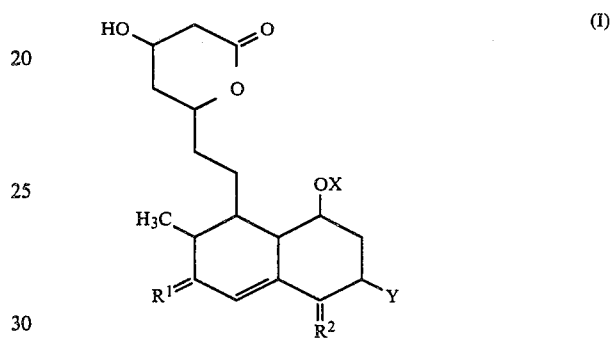

(I)

[wherein:

X represents a hydrogen atom or a 2-methylbutyryl group;

Y represents a hydrogen atom or a methyl group; and $R^1$ and $R^2$ are the same or different and each represents an oxygen atom or a group of formula $=N\text{-}OR^3$ (wherein $R^3$ represents a hydrogen atom or an alkyl group)], the free hydroxy-carboxylic acids corresponding thereto, that is to say compounds of formula (II):

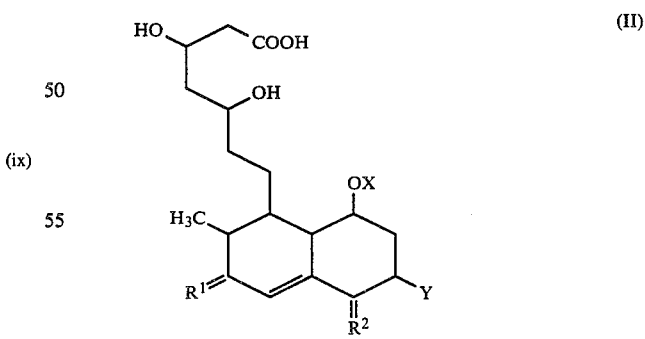

(II)

(wherein X, Y, $R^1$ and $R^2$ are as defined above) and salts and esters of said acids.

The invention also provides a process for preparing compounds of formula (I) in which $R^1$ and $R^2$ both represent oxygen atoms, that is to say compounds of formula (III):

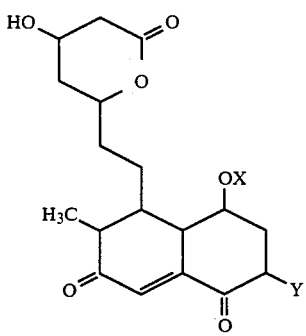

(III)

(wherein X and Y are as defined above) by reacting a compound of formula (IV):

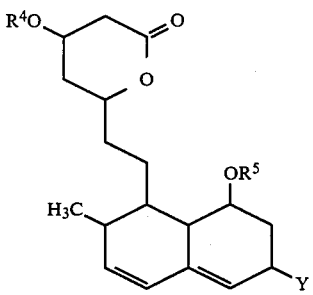

(IV)

(wherein Y is as defined above and $R^4$ and $R^5$ are the same or different and each represents a hydroxy-protecting group) with an oxidizing agent to give a compound of formula (V):

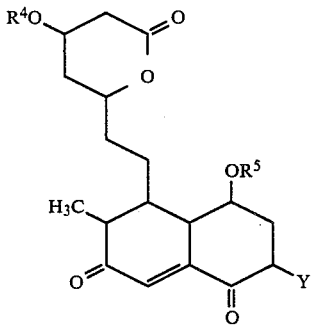

(V)

(wherein Y, $R^4$ and $R^5$ are as defined above), removing the hydroxy-protecting group represented by $R^4$ and, if necessary, removing that represented by $R^5$ (removal of the group represented by $R^5$ may not, of course, be necessary if $R^5$ represents a 2-methylbutyryl group).

Compounds of formula (I) in which one or both of the groups represented by $R^1$ and $R^2$ are groups of formula =N-$OR^3$, that is to say compounds of formula (VI):

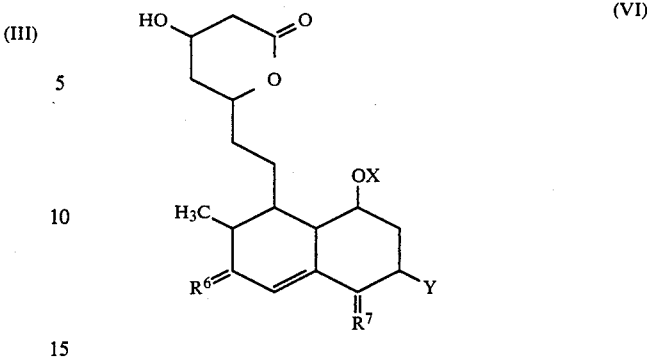

(VI)

[wherein X and Y are as defined above, and $R^6$ and $R^7$ are the same or different and each represents an oxygen atom or a group of formula =N-$OR^3$ (wherein $R^3$ is as defined above), provided that $R^6$ and $R^7$ do not both represent oxygen atoms], can be prepared by reacting the aforementioned compounds of formula (V) with an oximating agent of formula (XI):

$NH_2$-$OR^3$ (XI)

(wherein $R^3$ is as defined above), and then removing the protecting group represented by $R^4$ and, if necessary, removing the protecting group represented by $R^5$.

The above reactions provide the compounds of the invention in the form of the lactone; if desired, this may be subjected to a ring-opening reaction to give, depending upon the reagents chosen, the free acid, or a salt or ester of the free acid. If desired, the acid may be subjected to salification or esterification to give a salt or ester, the salt may be converted to the free acid or to an ester by conventional reactions and the ester may be deesterified to give the free acid or lactone.

DETAILED DESCRIPTION OF INVENTION

The compounds of formula (II) will form salts (hereinafter referred to as the "carboxylate salts") with the carboxylic acid group and such salts may be metal salts, ammonium salts or salts with organic amines or amino acids. Salts and esters of compounds of formula (II) in which one or both of $R^1$ and $R^2$ represents a group of formula =N-OH (i.e. a hydroxyimino group) will also form salts (hereinafter referred to as "hydroxyimino salts"), preferably with metal atoms.

The metal carboxylate salts of the present invention may be represented by formula (VII):

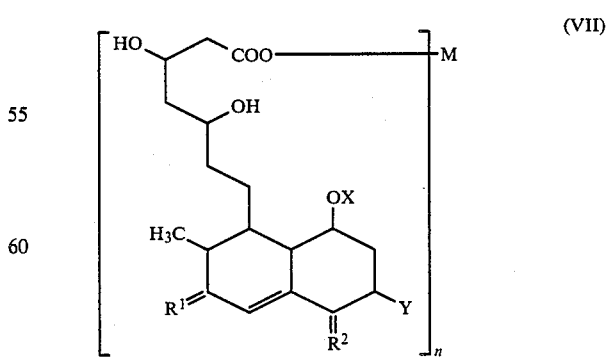

(VII)

in which $R^1$, $R^2$, X and Y are as defined above, M represents a metal atom and n represents the valency of the metal atom). Examples of metals which may be represented by M in these salts include: alkali metals, such as lithium, sodium or potassium; alkaline earth metals, such as calcium; and other metals, such as magnesium, aluminium, iron, zinc, nickel or cobalt. Of these metals, the alkali metals, alkaline earth metals and aluminium are preferred, sodium, potassium, calcium and aluminium being more preferred and sodium and potassium being most preferred.

The ammonium, organic amine and amino acid carboxylate salts of the compounds of the invention may be represented by formula (VIII):

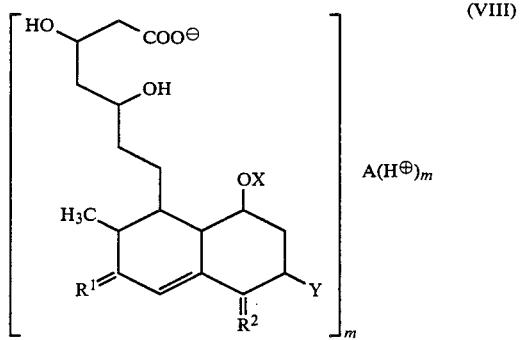
(VIII)

(in which $R^1$, $R^2$, X and Y are as defined above, A represents ammonia, an amino acid or an organic amine, and m is an integer). The integer represented by m is preferably 1, that is to say the amine or amino acid represented by A is preferably monoacidic.

Examples of amino acids which may be represented by A in the above formula (VIII) include such basic amino acids as arginine, lysine, histidine, 2,4-diaminobutyric acid or ornithine.

When A represents an organic amine, it is preferably a monoamine and may be an aliphatic, aromatic, alicyclic, heterocyclic or carbohydrate monoamine. Examples include: primary alkylamines, such as octylamine, t-octylamine or 2-ethylhexylamine; primary, secondary and tertiary $C_7$ or $C_8$ aralkylamines, such as benzylamine, α-methylbenzylamine, phenethylamine, dibenzylamine, N-methylbenzylamine, N,N- dimethylbenzylamine, N,N diethylbenzylamine, N ethyl-N-methylbenzylamine or tribenzylamine; primary, secondary or tertiary $C_5$-$C_7$ saturated alicyclic amines, such as cyclopentylamine cyclohexylamine, cycloheptylamine, N-methylcyclopentylamine, N-ethylcyclohexylamine, N-ethylcycloheptylamine, dicyclohexylamine, N,N dimethylcyclopentylamine, N,N dimethylcyclohexylamine or N,N diethylcycloheptylamine; 5 or 6 membered heterocyclic amines having a single nitrogen atom as the hetero atom, such as pyrrolidine, N-methylpyrrolidine, piperidine or N-methylpiperidine; morpholine; $C_1$-$C_3$ alkyl esters of aliphatic or aromatic amino acids , such as leucine methyl ester, diethyl glutamate, phenylglycine ethyl ester, β-penylalanine propyl ester or β-phenylalanine methyl ester; and amine derivatives of carbohydrates, such as glucosamine.

Where the amino acids and amines mentioned above can exist in the form of stereoisomers or optical isomers, it is possible to use any of the isomers or mixtures thereof.

Preferred amines are t-octylamine, benzylamine, dibenzylamine, N,N-dimethylbenzylamine, cyclohexylamine, dicyclohexylamine, N,N-dimethylcyclohexylamine, N-methylpyrrolidine, morpholine, L-leucine alkyl esters, dialkyl L-glutamates, D-phenylglycine alkyl esters and D-glucosamine; of which the most preferred amines are t-octylamine, dibenzylamine, dicyclohexylamine, morpholine, D-phenylglycine alkyl esters and D glucosamine.

It is also possible to form hydroxyimino salts of the carboxylate salts or esters of the compound of formula (II). These hydroxyimino salts are preferably salts with alkali metals (such as sodium or potassium) or alkaline earth metals (such as calcium) or with such other metals as magnesium. The alkali metal salts, especially the sodium or potassium salts, are preferred. In particular, the preferred hydroxyimino salts are salts of the compounds of formula (VII), given above, in which M represents an alkali metal, i.e. the alkali metal carboxylate salts, or of the compounds of formula (IX) given below, in which $R^8$ represents an alkyl group and p is 1, i.e. alkyl carboxylate esters.

The esters of the compounds of the invention may be represented by formula (IX):

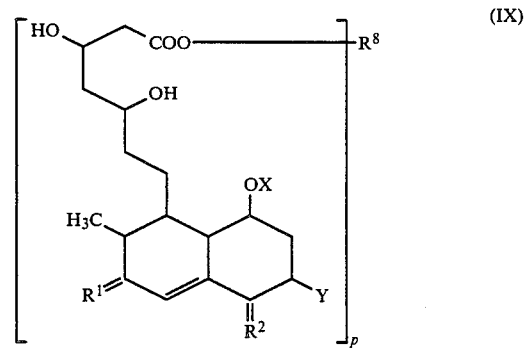
(IX)

(in which $R^1$, $R^2$, X and Y are as defined above, $R^8$ represents the alcoholic moiety of an ester and p represents the valency of $R^8$).

Where p represents 1, $R^8$ preferably represents an alkyl group, an unsubstituted benzyl group, a substituted benzyl group having at least one substituent selected from alkyl groups, alkoxy groups and halogen atoms, an unsubstituted phenacyl group or a substituted phenacyl group having at least one substituent selected from alkyl groups, alkoxy groups and halogen atoms.

Where $R^8$ represents an alkyl group, this may be a straight or branched chain group and preferably has from 1 to 6 carbon atoms. Examples of such a group include the methyl, ethyl, propyl, isopropyl, butyl, pentyl and hexyl groups.

Where $R^8$ represents a benzyl group, this may be unsubstituted or substituted, the substituents preferably being $C_1$ or $C_2$ alkyl or alkoxy groups or halogen atoms. One or more, preferably one, substituents are possible and, if there is more than one substituent, these may be the same or different. Examples of such benzyl groups include the benzyl, 2-methylbenzyl, 3-methylbenzyl, 4-methylbenzyl, 2-ethylbenzyl, 3-ethylbenzyl, 4-ethylbenzyl, 2-methoxybenzyl, 3-methoxybenzyl, 4-methoxybenzyl, 2-ethoxybenzyl, 3-ethoxybenzyl, 4-ethoxybenzyl, 2-chlorobenzyl, 3-chlorobenzyl, 4-chlorobenzyl, 2-bromobenzyl, 3-bromobenzyl and 4-bromobenzyl groups.

$R^8$ may represent an unsubstituted or substituted phenacyl group, in which the substituents are preferably $C_1$ or $C_2$ alkyl or alkoxy groups or halogen atoms. One or more, preferably one, substituents are possible and, where there is more than one substituent, these may be the same or different. Examples of such phenacyl groups include the phenacyl, 2-methylphenacyl, 3-methylphenacyl, 4-methylphenacyl, 2-ethylphenacyl, 3-ethylphenacyl, 4-ethylphenacyl, 2-methoxyphenacyl, 3-methoxyphenacyl, 4-methoxyphenacyl, 2-ethoxyphenacyl, 3-ethoxyphenacyl, 4-ethoxyphenacyl, 2-chlorophenacyl, 3-chlorophenacyl, 4-chlorophenacyl, 2-bromophenacyl, 3-bromophenacyl and 4-bromophenacyl groups.

Where p is 2, $R^8$ represents a bivalent alcoholic moiety, preferably a $C_2$-$C_6$ alkylene or alkylidene group, for example, an ethylene, ethylidene, propylene, propylidene, trimethylene, tetramethylene, butylidene, pentamethylene or pentylidene group, as well as such groups having one or more substituents, e.g. hydroxy groups, halogen atoms, or trifluoromethyl groups.

Where p is 3, $R^8$ represents a trivalent alcoholic moiety and it is preferably a saturated aliphatic hydrocarbon group having from 2 to 6 carbon atoms and optionally one or more substituents, e.g. hydroxy groups, halogen atoms or trifluoromethyl groups.

We prefer that p should be 1 and that $R^8$ should represent an alkyl group (most preferably methyl, ethyl, propyl, isopropyl, butyl, sec-butyl, t-butyl or hexyl), an optionally substituted benzyl group (most preferably benzyl, 4-methylbenzyl, 4-methoxybenzyl or 4-chlorobenzyl) or an optionally substituted phenacyl group (most preferably phenacyl, 4-methylphenacyl, 4-methoxyphenacyl or 4-bromophenacyl), most preferably an alkyl group, e.g, a methyl, ethyl, propyl, isopropyl, butyl, sec-butyl or t-butyl group, especially methyl or ethyl.

Where one or both $R^1$ and $R^2$ represents a group of formula $=N-OR^3$, $R^3$ may represent a hydrogen atom or an alkyl group. Where $R^3$ represents an alkyl group, this may be a straight or branched chain group and is preferably a lower alkyl group having from 1 to 6 carbon atoms, more preferably a methyl, ethyl, propyl, isopropyl, butyl, sec-butyl or t-butyl group, most preferably a methyl or ethyl group.

The compounds of the invention may exist in the form of various optical isomers, owing to the presence of asymmetric carbon atoms. Also, where one or both of $R^1$ and $R^2$ represents a group of formula $=N-OR^3$, syn and anti isomers are possible. Although all of these isomers are represented herein by a single plane formula, it will be understood that the present invention contemplates both the individual isomers and mixtures thereof.

Examples of compounds of the invention are listed below. A semi-systematic system of nomenclature is employed, in which the compounds are named as derivatives of IsoML-236A, IsoML-236B, IsoMB-530B or IsoMB-530A, which have the structures shown in formulae (vi)–(ix), respectively. The positions of substituents are identified by the numbers shown on formula (v) and the naming of substituents follows the recommendations of the International Union of Pure and Applied Chemistry (IUPAC) Commission on the Nomenclature of Organic Chemistry, as published in "Nomenclature of Organic Chemistry, Sections A,B,C,D,E,F and H", published by Pergamon Press, Oxford, England (1979).

1. 3,4-Dihydro-6-oxo-4-hydroxyiminoIsoML-236A lactone.
2. 3,4-Dihydro-6-oxo-4-hydroxyiminoIsoML-236B lactone.
3. 3,4-Dihydro-6-oxo-4-hydroxyiminoIsoMB-530A lactone.
4. 3,4-Dihydro-6-oxo-4-hydroxyiminoIsoMB-530B lactone.
5. 3,4-Dihydro-6-oxo-4-methoxyiminoIsoML-236A lactone.
6. 3,4-Dihydro-6-oxo-4-methoxyiminoIsoML-236B lactone.
7. 3,4-Dihydro-6-oxo-4-methoxyiminoIsoMB-530A lactone.
8. 3,4-Dihydro-6-oxo-4-methoxyiminoIsoMB-530B lactone.
9. 3,4-Dihydro-6-oxo-4-ethoxyiminoIsoML-236A lactone.
10. 3,4-Dihydro-6-oxo-4-ethoxyiminoIsoML-236B lactone.
11. 3,4-Dihydro-6-oxo-4-ethoxyiminoIsoMB-530A lactone.
12. 3,4-Dihydro-6-oxo-4-ethoxyiminoIsoMB-530B lactone.
13. Sodium 3,4-dihydro-6-oxo-4-hydroxyiminoIsoML-236A carboxylate.
14. Sodium 3,4-dihydro-6-oxo-4-hydroxyiminoIsoML-236B carboxylate.
15. Sodium 3,4-dihydro-6-oxo-4-hydroxyiminoIsoMB-530A carboxylate.
16. Sodium 3,4-dihydro-6-oxo-4-hydroxyiminoIsoMB-530B carboxylate.
17. Potassium 3,4-dihydro-6-oxo-4-hydroxyiminoIsoML-236A carboxylate.
18. Potassium 3,4-dihydro-6-oxo-4-hydroxyiminoIsoML-236B carboxylate.
19. Potassium 3,4-dihydro-6-oxo-4-hydroxyiminoIsoMB-530A carboxylate.
20. Potassium 3,4-dihydro-6-oxo-4-hydroxyiminoIsoMB-530B carboxylate.
21. Methyl 3,4-dihydro-6-oxo-4-hydroxyiminoIsoML-236A carboxylate.
22. Methyl 3,4-dihydro-6-oxo-4-hydroxyiminoIsoML-236B carboxylate.
23. Methyl 3,4-dihydro-6-oxo-4-hydroxyiminoIsoMB-530A carboxylate.
24. Methyl 3,4-dihydro-6-oxo-4-hydroxyiminoIsoMB-530B carboxylate.
25. Disodium 3,4-dihydro-6-oxo-4-oxidoiminoIsoML-236A carboxylate.
26. Disodium 3,4-dihydro-6-oxo-4-oxidoiminoIsoML-236B carboxylate.
27. Disodium 3,4-dihydro-6-oxo-4-oxidoiminoIsoMB-530A carboxylate.
28. Disodium 3,4-dihydro-6-oxo-4-oxidoiminoIsoMB-530B carboxylate.
29. Sodium 3,4-dihydro-6-oxo-4-methoxyiminoIsoML-236A carboxylate.
30. Sodium 3,4-dihydro-6-oxo-4-methoxyiminoIsoML-236B carboxylate.
31. Sodium 3,4-dihydro-6-oxo-4-methoxyiminoIsoMB-530A carboxylate.
32. Sodium 3,4-dihydro-6-oxo-4-methoxyiminoIsoMB-530B carboxylate.
33. Potassium 3,4-dihydro-6-oxo-4-methoxyiminoIsoML-236A carboxylate.
34. Potassium 3,4-dihydro-6-oxo-4-methoxyiminoIsoML-236B carboxylate.
35. Potassium 3,4-dihydro-6-oxo-4-methoxyiminoIsoMB-530A carboxylate.
36. Potassium 3,4-dihydro-6-oxo-4-methoxyiminoIsoMB-530B carboxylate.
37. Methyl 3,4-dihydro-6-oxo-4-methoxyiminoIsoML-236A carboxylate.

38. Methyl 3,4-dihydro-6-oxo-4-methoxyiminoIsoML-236B carboxylate.
39. Methyl 3,4-dihydro-6-oxo-4-methoxyiminoIsoMB-530A carboxylate.
40. Methyl 3,4-dihydro-6-oxo-4-methoxyiminoIsoMB-530B carboxylate.
41. Sodium 3,4-dihydro-6-oxo-4-ethoxyiminoIsoML-236A carboxylate.
42. Sodium 3,4-dihydro-6-oxo-4-ethoxyiminoIsoML-236B carboxylate.
43. Sodium 3,4-dihydro-6-oxo-4-ethoxyiminoIsoMB-530A carboxylate.
44. Sodium 3,4-dihydro-6-oxo-4-ethoxyiminoIsoMB-530B carboxylate.
45. Potassium 3,4-dihydro-6-oxo-4-ethoxyiminoIsoML-236A carboxylate.
46. Potassium 3,4-dihydro-6-oxo-4-ethoxyiminoIsoML-236B carboxylate.
47. Potassium 3,4-dihydro-6-oxo-4-ethoxyiminoIsoMB-530A carboxylate.
48. Potassium 3,4-dihydro-6-oxo-4-ethoxyiminoIsoMB-530B carboxylate.
49. Methyl 3,4-dihydro-6-oxo-4-ethoxyiminoIsoML-236A carboxylate.
50. Methyl 3,4-dihydro-6-oxo-4-ethoxyiminoIsoML-236B carboxylate.
51. Methyl 3,4-dihydro-6-oxo-4-ethoxyiminoIsoMB-530A carboxylate.
52. Methyl 3,4-dihydro-6-oxo-4-ethoxyiminoIsoMB-530B carboxylate.
53. Dipotassium 3,4-dihydro-6-oxo-4-oxidoiminoIsoML-236A carboxylate.
54. Dipotassium 3,4-dihydro-6-oxo-4-oxidoiminoIsoML-236B carboxylate.
55. Dipotassium 3,4-dihydro-6-oxo-4-oxidoiminoIsoMB-530A carboxylate.
56. Dipotassium 3,4-dihydro-6-oxo-4-oxidoiminoIsoMB-530B carboxylate.
57. 3,4-Dihydro-4-oxo-6-hydroxyiminoIsoML-236A lactone.
58. 3,4-Dihydro-4-oxo-6-hydroxyiminoIsoML-236B lactone.
59. 3,4-Dihydro-4-oxo-6-hydroxyiminoIsoMB-530A lactone.
60. 3,4-Dihydro-4-oxo-6-hydroxyiminoIsoMB-530B lactone.
61. 3,4-Dihydro-4-oxo-6-methoxyiminoIsoML-236A lactone.
62. 3,4-Dihydro-4-oxo-6-methoxyiminoIsoML-236B lactone.
63. 3,4-Dihydro-4-oxo-6-methoxyiminoIsoMB-530A lactone.
64. 3,4-Dihydro-4-oxo-6-methoxyiminoIsoMB-530B lactone,
65. 3,4-Dihydro-4-oxo-6-ethoxyiminoIsoML-236A lactone.
66. 3,4-Dihydro-4-oxo-6-ethoxyiminoIsoML-236B lactone.
67. 3,4-Dihydro-4-oxo-6-ethoxyiminoIsoMB-530A lactone.
68. 3,4-Dihydro-4-oxo-6-ethoxyiminoIsoMB-530B lactone.
69. Sodium 3,4-dihydro-4-oxo-6-hydroxyiminoIsoML-236A carboxylate.
70. Sodium 3,4-dihydro-4-oxo-6-hydroxyiminoIsoML-236B carboxylate.
71. Sodium 3,4-dihydro-4-oxo-6-hydroxyiminoIsoMB-530A carboxylate.
72. Sodium 3,4-dihydro-4-oxo-6-hydroxyiminoIsoMB-530B carboxylate.
73. Potassium 3,4-dihydro-4-oxo-6-hydroxyiminoIsoML-236A carboxylate.
74. Potassium 3,4-dihydro-4-oxo-6-hydroxyiminoIsoML-236B carboxylate.
75. Potassium 3,4-dihydro-4-oxo-6-hydroxyiminoIsoMB-530A carboxylate.
76. Potassium 3,4-dihydro-4-oxo-6-hydroxyiminoIsoMB-530B carboxylate.
77. Methyl 3,4-dihydro-4-oxo-6-hydroxyiminoIsoML-236A carboxylate.
78. Methyl 3,4-dihydro-4-oxo-6-hydroxyiminoIsoML-236B carboxylate.
79. Methyl 3,4-dihydro-4-oxo-6-hydroxyiminoIsoMB-530A carboxylate.
80. Methyl 3,4-dihydro-4-oxo-6-hydroxyiminoIsoMB-530B carboxylate.
81. Disodium 3,4-dihydro-4-oxo-6-oxidoiminoIsoML-236A carboxylate.
82. Disodium 3,4-dihydro-4-oxo-6-oxidoiminoIsoML-236B carboxylate.
83. Disodium 3,4-dihydro-4-oxo-6-oxidoiminoIsoMB-530A carboxylate.
84. Disodium 3,4-dihydro-4-oxo-6-oxidoiminoIsoMB-530B carboxylate.
85. Sodium 3,4-dihydro-4-oxo-6-methoxyiminoIsoML-236A carboxylate.
86. Sodium 3,4-dihydro-4-oxo-6-methoxyiminoIsoML-236B carboxylate.
87. Sodium 3,4-dihydro-4-oxo-6-methoxyiminoIsoMB-530A carboxylate.
88. Sodium 3,4-dihydro-4-oxo-6-methoxyiminoIsoMB-530B carboxylate.
89. Potassium 3,4-dihydro-4-oxo-6-methoxyiminoIsoML-236A carboxylate.
90. Potassium 3,4-dihydro-4-oxo-6-methoxyiminoIsoML-236B carboxylate.
91. Potassium 3,4-dihydro-4-oxo-6-methoxyiminoIsoMB-530A carboxylate.
92. Potassium 3,4-dihydro-4-oxo-6-methoxyiminoIsoMB-530B carboxylate.
93. Methyl 3,4-dihydro-4-oxo-6-methoxyiminoIsoML-236A carboxylate.
94. Methyl 3,4-dihydro-4-oxo-6-methoxyiminoIsoML-236B carboxylate.
95. Methyl 3,4-dihydro-4-oxo-6-methoxyiminoIsoMB-530A carboxylate.
96. Methyl 3,4-dihydro-4-oxo-6-methoxyiminoIsoMB-530B carboxylate.
97. Sodium 3,4-dihydro-4-oxo-6-ethoxyiminoIsoML-236A carboxylate.
98. Sodium 3,4-dihydro-4-oxo-6-ethoxyiminoIsoML-236B carboxylate.
99. Sodium 3,4-dihydro-4-oxo-6-ethoxyiminoIsoMB-530A carboxylate.
100. Sodium 3,4-dihydro-4-oxo-6-ethoxyiminoIsoMB-530B carboxylate.
101. Potassium 3,4-dihydro-4-oxo-6-ethoxyiminoIsoML-236A carboxylate.
102. Potassium 3,4-dihydro-4-oxo-6-ethoxyiminoIsoML-236B carboxylate.
103. Potassium 3,4-dihydro-4-oxo-6-ethoxyiminoIsoMB-530A carboxylate.
104. Potassium 3,4-dihydro-4-oxo-6-ethoxyiminoIsoMB-530B carboxylate.
105. Methyl 3,4-dihydro-4-oxo-6-ethoxyiminoIsoML-236A carboxylate.

106. Methyl 3,4-dihydro-4-oxo-6-ethoxyiminoIsoML-236B carboxylate.
107. Methyl 3,4-dihydro-4-oxo-6-ethoxyiminoIsoMB-530A carboxylate.
108. Methyl 3,4-dihydro-4-oxo-6-ethoxyiminoIsoMB-530B carboxylate.
109. Dipotassium 3,4-dihydro-4-oxo-6-oxidoiminoIsoML-236A carboxylate.
110. Dipotassium 3,4-dihydro-4-oxo-6-oxidoiminoIsoML-236B carboxylate.
111. Dipotassium 3,4-dihydro-4-oxo-6-oxidoiminoIsoMB-530A carboxylate.
112. Dipotassium 3,4-dihydro-4-oxo-6-oxidoiminoIsoMB-530B carboxylate.
113. 3,4-Dihydro-4,6-bis(hydroxyimino)IsoML-236A lactone.
114. 3,4-Dihydro 4,6-bis(hydroxyimino)IsoML-236B lactone.
115. 3,4-Dihydro-4,6-bis(hydroxyimino)IsoMB-530A lactone.
116. 3,4-Dihydro-4,6-bis(hydroxyimino)IsoMB-530B lactone.
117. 3,4-Dihydro-4,6-bis(methoxyimino)IsoML-236A lactone.
118. 3,4-Dihydro-4,6-bis(methoxyimino)IsoML-236B lactone.
119. 3,4-Dihydro-4,6-bis(methoxyimino)IsoMB-530A lactone.
120. 3,4-Dihydro-4,6-bis(methoxyimino)IsoMB-530B lactone.
121. 3,4-Dihydro-4,6-bis(ethoxyimino)IsoML-236A lactone.
122. 3,4-Dihydro-4,6-bis(ethoxyimino)IsoML-236B lactone.
123. 3,4-Dihydro-4,6-bis(ethoxyimino)IsoMB-530A lactone.
124. 3,4-Dihydro-4,6-bis(ethoxyimino)IsoMB-530B lactone.
125. Sodium 3,4-dihydro-4,6-bis(hydroxyimino)IsoML-236A carboxylate.
126. Sodium 3,4-dihydro-4,6-bis(hydroxyimino)IsoML-236B carboxylate.
127. Sodium 3,4-dihydro-4,6-bis(hydroxyimino)IsoMB-530A carboxylate.
128. Sodium 3,4-dihydro-4,6-bis(hydroxyimino)IsoMB-530B carboxylate.
129. Potassium 3,4-dihydro-4,6-bis(hydroxyimino)IsoML-236A carboxylate.
130. Potassium 3,4-dihydro-4,6-bis(hydroxyimino)IsoML-236B carboxylate.
131. Potassium 3,4-dihydro-4,6-bis(hydroxyimino)IsoMB-530A carboxylate.
132. Potassium 3,4-dihydro-4,6-bis(hydroxyimino)IsoMB-530B carboxylate.
133. Methyl 3,4-dihydro-4,6-bis(hydroxyimino)IsoML-236A carboxylate.
134. Methyl 3,4-dihydro-4,6-bis(hydroxyimino)IsoML-236B carboxylate.
135. Methyl 3,4-dihydro-4,6-bis(hydroxyimino)IsoMB-530A carboxylate.
136. Methyl 3,4-dihydro-4,6-bis(hydroxyimino)IsoMB-530B carboxylate.
137. Trisodium 3,4-dihydro-4,6-bis(oxidoimino)IsoML-236A carboxylate.
138. Trisodium 3,4-dihydro-4,6-bis(oxidoimino)IsoML-236B carboxylate.
139. Trisodium 3,4-dihydro-4,6-bis(oxidoimino)IsoMB-530A carboxylate.
140. Trisodium 3,4-dihydro-4,6-bis(oxidoimino)IsoMB-530B carboxylate.
141. Sodium 3,4-dihydro-4,6-bis(methoxyimino)IsoML-236A carboxylate.
142. Sodium 3,4-dihydro-4,6-bis(methoxyimino)IsoML-236B carboxylate.
143. Sodium 3,4-dihydro-4,6-bis(methoxyimino)IsoMB-530A carboxylate.
144. Sodium 3,4-dihydro-4,6-bis(methoxyimino)IsoMB-530B carboxylate.
145. Potassium 3,4-dihydro-4,6-bis(methoxyimino)IsoML-236A carboxylate.
146. Potassium 3,4-dihydro-4,6-bis(methoxyimino)IsoML-236B carboxylate.
147. Potassium 3,4-dihydro-4,6-bis(methoxyimino)IsoMB-530A carboxylate.
148. Potassium 3,4-dihydro-4,6-bis(methoxyimino)IsoMB-530B carboxylate.
149. Methyl 3,4-dihydro-4,6-bis(methoxyimino)IsoML-236A carboxylate.
150. Methyl 3,4-dihydro-4,6-bis(methoxyimino)IsoML-236B carboxylate.
151. Methyl 3,4-dihydro-4,6-bis(methoxyimino)IsoMB-530A carboxylate.
152. Methyl 3,4-dihydro-4,6-bis(methoxyimino)IsoMB-530B carboxylate.
153. Sodium 3,4-dihydro-4,6-bis(ethoxyimino)IsoML-236A carboxylate.
154. Sodium 3,4-dihydro-4,6-bis(ethoxyimino)IsoML-236B carboxylate.
155. Sodium 3,4-dihydro-4,6-bis(ethoxyimino)IsoMB-530A carboxylate.
156. Sodium 3,4-dihydro-4,6-bis(ethoxyimino)IsoMB-530B carboxylate.
157. Potassium 3,4-dihydro-4,6-bis(ethoxyimino)IsoML-236A carboxylate.
158. Potassium 3,4-dihydro-4,6-bis(ethoxyimino)IsoML-236B carboxylate.
159. Potassium 3,4-dihydro-4,6-bis(ethoxyimino)IsoMB-530A carboxylate.
160. Potassium 3,4-dihydro-4,6-bis(ethoxyimino)IsoMB-530B carboxylate.
161. Methyl 3,4-dihydro-4,6-bis(ethoxyimino)IsoML-236A carboxylate.
162. Methyl 3,4-dihydro-4,6-bis(ethoxyimino)IsoML-236B carboxylate.
163. Methyl 3,4-dihydro-4,6-bis(ethoxyimino)IsoMB-530A carboxylate.
164. Methyl 3,4-dihydro-4,6-bis(ethoxyimino)IsoMB-530B carboxylate.
165. Tripotassium 3,4-dihydro-4,6-bis(oxidoimino)IsoML-236A carboxylate.
166. Tripotassium 3,4-dihydro-4,6-bis(oxidoimino)IsoML-236B carboxylate.
167. Tripotassium 3,4-dihydro-4,6-bis(oxidoimino)IsoMB-530A carboxylate.
168. Tripotassium 3,4-dihydro-4,6-bis(oxidoimino)IsoMB-530B carboxylate.
169. 3,4-Dihydro-4-hydroxyimino-6-methoxyiminoIsoML-236B lactone.
170. 3,4-Dihydro-4-hydroxyimino-6-methoxyiminoIsoMB-530B lactone.
171. 3,4-Dihydro-4-hydroxyimino-6-ethoxyiminoIsoML-236B lactone.
172. 3,4-Dihydro-4-hydroxyimino-6-ethoxyiminoIsoMB-530B lactone.
173. Sodium 3,4-dihydro-4-hydroxyimino-6-methoxyimino-IsoML-236B carboxylate.

174. Sodium 3,4-dihydro-4-hydroxyimino-6-methoxyimino-IsoMB-530B carboxylate.
175. Potassium 3,4-dihydro-4-hydroxyimino-6-methoxyiminoIsoML-236B carboxylate.
176. Potassium 3,4-dihydro-4-hydroxyimino-6-methoxyiminoIsoMB-530B carboxylate.
177. Disodium 3,4-dihydro-4-oxoimino-6-methoxyiminoIsoML-236B carboxylate.
178. Disodium 3,4-dihydro-4-oxoimino-6-methoxyiminoIsoMB-530B carboxylate.
179. Disodium 3,4-dihydro-4-oxoimino-6-ethoxyiminoIsoML-236B carboxylate.
180. Disodium 3,4-dihydro-4-oxoimino-6-ethoxyiminoIsoMB-530B carboxylate.
181. 3,4-Dihydro-6-hydroxyimino-4-methoxyiminoIsoML-236B lactone.
182. 3,4-Dihydro-6-hydroxyimino-4-methoxyiminoIsoMB-530B lactone.
183. 3,4-Dihydro-6-hydroxyimino-4-ethoxyiminoIsoML-236B lactone.
184. 3,4-Dihydro-6-hydroxyimino-4-ethoxyiminoIsoMB-530B lactone.
185. Sodium 3,4-dihydro-6-hydroxyimino-4-methoxyiminoIsoML-236B carboxylate.
186. Sodium 3,4-dihydro-6-hydroxyimino-4-methoxyiminoIsoMB-530B carboxylate.
187. Potassium 3,4-dihydro-6-hydroxyimino-4-methoxyiminoIsoML-236B carboxylate.
188. Potassium 3,4-dihydro-6-hydroxyimino-4-methoxyiminoIsoMB-530B carboxylate.
189. Sodium 3,4-dihydro-6-hydroxyimino-4-ethoxyiminoIsoML-236B carboxylate.
190. Sodium 3,4-dihydro-6-hydroxyimino-4-ethoxyiminoIsoMB-530B carboxylate.
191. Potassium 3,4-dihydro-6-hydroxyimino-4-ethoxyiminoIsoML-236B carboxylate.
192. Potassium 3,4-dihydro-6-hydroxyimino-4-ethoxyiminoIsoMB-530B carboxylate.
193. Disodium 3,4-dihydro-6-oxidoimino-4-methoxyiminoIsoML-236B carboxylate.
194. Disodium 3,4-dihydro-6-oxidoimino-4-methoxyiminoIsoMB-530B carboxylate.
195. Disodium 3,4-dihydro-6-oxidoimino-4-ethoxyiminoIsoML-236B carboxylate.
196. Disodium 3,4-dihydro-6-oxidoimino-4-ethoxyiminoIsoMB-530B carboxylate.
197. 3,4-Dihydro-6-oxo-4-propoxyiminoIsoML-236A lactone.
198. 3,4-Dihydro-6-oxo-4-propoxyiminoIsoML-236B lactone.
199. 3,4-Dihydro-6-oxo-4-propoxyiminoIsoMB-530A lactone.
200. 3,4-Dihydro-6-oxo-4-propoxyiminoIsoMB-530B lactone.
201. Sodium 3,4-dihydro-6-oxo-4-propoxyiminoIsoML-236A carboxylate.
202. Sodium 3,4-dihydro-6-oxo-4-propoxyiminoIsoML-236B carboxylate.
203. Sodium 3,4-dihydro-6-oxo-4-propoxyiminoIsoMB-530A carboxylate.
204. Sodium 3 4-dihydro-6-oxo-4-propoxyiminoIsoMB-530B carboxylate.
205. Potassium 3,4-dihydro-6-Oxo-4-propoxyiminoIsoML-236A carboxylate.
206. Potassium 3,4-dihydro-6-oxo-4-propoxyiminoIsoML-236B carboxylate.
207. Potassium 3,4-dihydro-6-oxo-4-propoxyiminoIsoMB-530A carboxylate.
208. Potassium 3,4-dihydro-6-oxo-4-propoxyiminoIsoMB-530B carboxylate.
209. Ethyl 3,4-dihydro-6-oxo-4-propoxyiminoIsoML-236A carboxylate.
210. Ethyl 3,4-dihydro-6-oxo-4-propoxyiminoIsoML-236B carboxylate.
211. Ethyl 3,4-dihydro-6-oxo-4-propoxyiminoIsoMB-530A carboxylate.
212. Ethyl 3,4-dihydro-6-oxo-4-propoxyiminoIsoMB-530B carboxylate.

The compounds of the invention may be prepared by the processes summarised in the following reaction scheme:

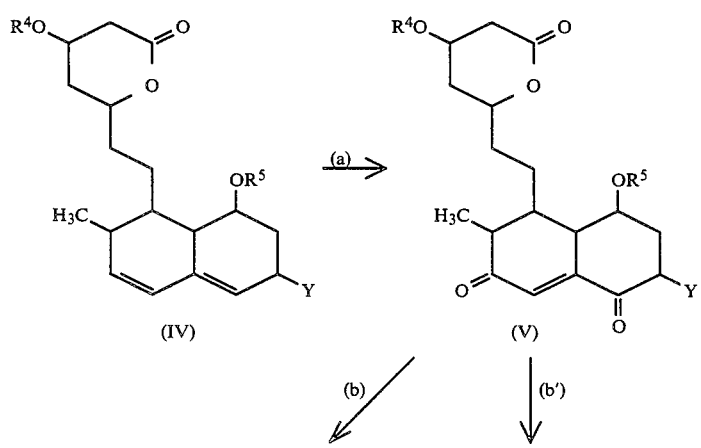

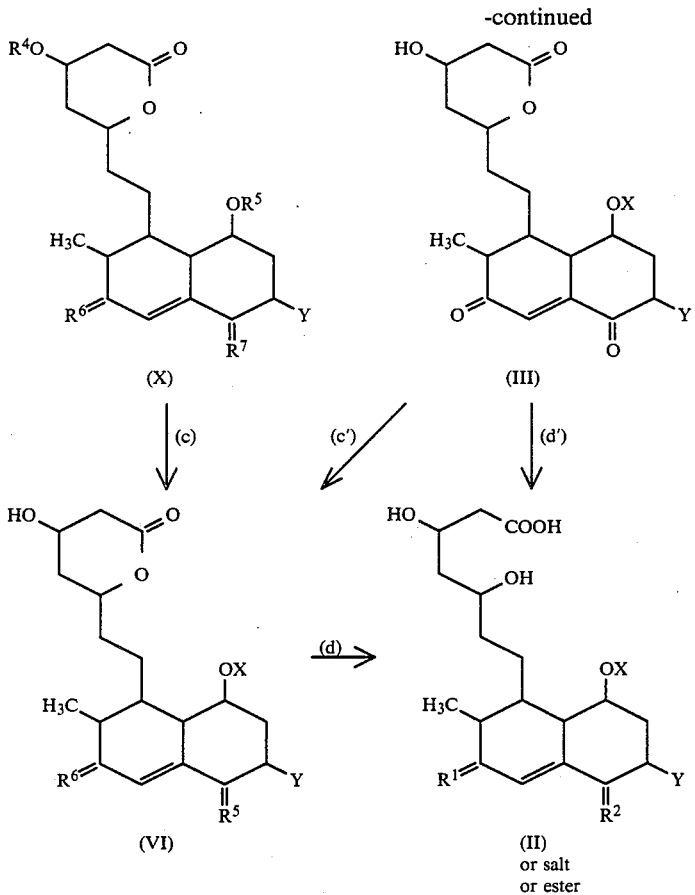

In the above formulae, $R^1$, $R^2$, $R^4$, $R^5$, $R^6$, $R^7$, x and Y are as defined above.

The first step, step (a), comprises oxidising a compound of formula (IV) with a suitable oxidising agent, to give a compound of formula (V). This reaction is preferably effected in the presence of a solvent, the nature of which is not critical, provided that it has no adverse effect on the reaction. Examples of suitable solvents include: halogenated hydrocarbons, such as methylene chloride, ethylene chloride or chloroform; and N,N-dialkyl fatty acid amides, such as dimethylformamide or dimethylacetamide; of these, we prefer methylene chloride or dimethylformamide. The oxidising agent employed in this reaction is preferably a chromium (III) compound, for example a complex of chromic anhydride with an organic base [such as chromic anhydride/pyridine (Collins' reagent)], pyridinium dichromate or pyridinium chlorochromate, most preferably chromic anhydride/pyridine. The reaction temperature may range from −10° C. to +50° C., preferably from 0° C. to ambient temperature. The time allowed for the reaction is usually from 1 to 30 hours, preferably from 10 to 15 hours.

In step (b) of the reaction scheme, the dione compound of formula (V) is contacted with an oximating agent of formula (XI):

$$NH_2OR^3 \qquad (XI)$$

(in which $R^3$ represents a hydrogen atom or an alkyl group), normally in the presence of a solvent. The nature of the solvent is not critical, provided that it has no adverse effect on the reaction. Suitable solvents include: alcohols, such as methanol, ethanol or propanol; ethers, such as diethyl ether, tetrahydrafuran or dioxane; and mixtures of water with one or more of these solvents. The reaction may be promoted by the presence of a base, for example: a tertiary alkylamine (e.g. triethylamine or tributylamine); an aromatic amine (e.g. pyridine or lutidine); an alkali metal acetate (e.g. sodium acetate or potassium acetate); or an alkali metal carbonate or bicarbonate (e.g. sodium bicarbonate, sodium carbonate or potassium carbonate); of these, we prefer triethylamine, pyridine or sodium acetate. The oximating agent of formula (XI) may be used as such or in the form of a salt with a mineral acid, for example hydrochloric acid, nitric acid or sulphuric acid. We particularly prefer to use those compounds of formula (XI) in which $R^3$ represents a hydrogen atom or a methyl or ethyl group, or a hydrochloride of such a compound.

Since the compound of formula (V) contains two oxo groups, either one or both of the two possible mono-oxime compounds (in which $R^6$ represents an oxygen atom and $R^7$ represents a group of formula $=N-OR^3$, or in which $R^6$ represents a group of formula $=N-OR^3$ and $R^7$ represents an oxygen atom) or a dioxime compound (in which both $R^6$ and $R^7$ represent groups of formula $=N-OR^3$) may be prepared by controlling the amount of oximating agent. Specifically, the mono-oxime compounds can be prepared as the main product by using from 1 to 1.5 equivalents of oximating agent per mole of said compound of formula (V); on the other hand, the dioxime compound can be prepared as the main product by using from 2 to 3 equivalents of oximating agent per mole of said compound of formula (V). The reaction may be conducted over a wide temperature range, e.g. from −10° C. to +100° C., but the reaction temperature is preferably from 0° C. to 50° C. The time allowed for the reaction is normally from 30 minutes to 10 hours, preferably from 1 to 5 hours.

After completion of either or both of steps (a) and (b), the resulting compound from each step may be recovered from the reaction mixture by conventional means. For example, the reaction mixture may be diluted with a water-immiscible solvent and washed with water, after which the solvent is removed by distillation, to give the desired compound. This compound may, if necessary, be further purified by conventional means, for example by recrystallisation, reprecipitation or the various chromatographic techniques, particularly column chromatography.

In step (c) of the above reaction scheme, the hydroxy-protecting group represented by $R^4$ and, if desired, the hydroxy-protecting group represented by $R^5$ may be removed to give the desired compound of formula (VI) containing one or two hydroxy groups (where the group represented by $R^5$ is a 2-methylbutyryl group, then, of course, this group need not be removed). Similarly, in step (b'), one or both of the protecting groups represented by $R^4$ and $R^5$ may be removed to give the compound of formula (III). The nature of the reaction employed to remove the protecting group or groups will, of course, depend upon the nature of such groups and any hydroxy-protecting groups known in the art may be used, provided that the reactions required to remove them do not adversely affect other parts of the molecule.

For example, the protecting group may be a tri(lower alkyl)silyl group, for example a trimethylsilyl or t-butyldimethylsilyl group. In this case, the protecting group may be removed by treating the compound of formula (X) or (V) with a compound providing fluoride ions, such as tetrabutylammonium fluoride, or with an acid, such as trichloroacetic acid or trifluoroacetic acid, preferably with a compound capable of providing fluoride ions. This reaction is preferably carried out in the presence of a solvent, the nature of which is not critical provided that it has no adverse effect upon the reaction; suitable solvents include ethers, such as tetrahydrofuran or dioxane. Where the reaction is effected using a compound capable of providing fluoride ions, the reaction may be promoted by the addition of a fatty acid, such as acetic acid or propionic acid. The reaction is preferably carried out at about ambient temperature and will normally require from 10 to 18 hours.

Another suitable protecting group is the tetrahydropyranyl group. In this case, the group may be removed by treating the compound of formula (X) or (V) with a catalytic amount of an acid, such as hydrochloric acid, nitric acid, sulphuric acid or p-toluenesulphonic acid. The reaction is preferably effected in the presence of a solvent, the nature of which is not critical provided that it has no adverse effect upon the reaction; the solvent is preferably an organic solvent, such as acetic acid, methanol, ethanol or tetrahydrofuran, or a mixture of one or more of these organic solvents with water. The reaction is preferably effected at about ambient temperature and will normally require from 1 to 5 hours.

Other suitable protecting groups include the halogenated alkyl groups, such as the 2,2-dibromoethyl or 2,2,2-trichloroethyl groups. In this case, the protecting group may be removed by contacting the compound of formula (X) or (V) with zinc in the presence of an alcohol, such as methanol or ethanol.

Of the protecting groups described above, the most preferred group is the t-butyldimethylsilyl group.

The desired compound of formula (VI) or (III) obtained by elimination of one or both hydroxy-protecting groups as described above can be recovered from the reaction mixture by conventional means and, if necessary, further purified by well known techniques, such as recrystallisation or the various chromatographic techniques, especially preparative thin layer chromatography or column chromatography.

If desired, the compound of formula (VI) may also be prepared by step (c'), in which the compound of formula (III) is oximated using an oximating agent of formula (XI), as described above. The reagents and reaction conditions are similar to those described in relation to step (b). However, this sequence for preparing the compound of formula (VI) is less preferred than the sequence culminating in step (c), since the product and starting material in step (c'), that is the compounds of formulae (VI) and (III), have similar Rf values on thin layer chromatography and it is, therefore, difficult to isolate the product.

The compounds of formulae (III) and (VI) can, if necessary, be converted to the metal carboxylate salt or carboxylate ester of the carboxylic acid of formula (II), in which the lactone ring has been opened, by hydrolysis or solvolysis respectively.

The metal carboxylic salt can be obtained by subjecting the compound of formula (III) or (VI) to a conventional hydrolysis reaction, for example, simply by contacting the compound with an alkali metal hydroxide (such as sodium hydroxide or potassium hydroxide) in water or in an aqueous organic solvent, such as an aqueous alcohol, aqueous acetone or aqueous dioxane. The alkali metal hydroxide is preferably employed in an amount of from 1 to 1.5 moles per mole of said compound formula (III) or (VI). The reaction is preferably effected at about ambient temperature and the time allowed for the reaction is preferably from 1 to 5 hours.

After completion of the reaction, the desired compound may be recovered from the reaction mixture by conventional means. For example, the solvent may be removed by distillation under reduced pressure and the residue freeze-dried to give the desired metal carboxylate salt, which can, if necessary, be further purified by such conventional techniques as recrystallization or the various chromatographic techniques, especially column chromatography.

The carboxylate ester can be obtained by subjecting the lactone of formula (III) or (VI) to a conventional solvolysis reaction, for example by contacting the compound with an alcohol (such as methanol, ethanol, propanol or isopropanol) in the presence of an acid catalyst, for example a mineral acid (e.g. hydrochloric acid or sulphuric acid), a Lewis acid (e.g. boron trifluoride) or an acidic ion-exchange resin. The reaction may, if desired, be carried out in the presence of an inert organic solvent (for example benzene, diethyl ether or chloroform), but it is preferred to use the alcohol itself as the reaction solvent. The reaction is preferably carried out with heating, for example, at an elevated temperature which may range from 50° C. to the reflux temperature of the solvent employed. Several hours should usually be allowed for the reaction.

After completion of the reaction, the desired compound may be recovered from the reaction mixture by conventional means. For example, where an ion-exchange resin is used as the catalyst, it is removed by filtration and the solvent is distilled from the filtrate to give the desired compound. Where a mineral acid or a Lewis acid is used, the reaction mixture is first neutralized, the solvent is then distilled off, the residue is extracted with an appropriate solvent and then the solvent is distilled from the extract to give the desired compound. The resulting compound may then, if required, be further purified by conventional means, for example the various chromagraphic techniques, especially column chromatography.

If desired, it is also possible to carry out the aforementioned hydrolysis or solvolysis reactions at any point in the above reaction scheme after step (a); in other words, any of compounds (V), (X), (VI) and (III) may be subjected to this hydrolysis or solvolysis reaction to give the corresponding salt or ester and this salt or ester may, if required, be subjected to a subsequent reaction as in steps (b), (c), (b') or (c'), as described above, to give the salts or esters corresponding to the lactones shown in the reaction scheme. In theory, it is also possible to start the reaction scheme by employing a salt or ester corresponding to the compound of formula (IV), but this is not preferred, as it is then necessary to protect the free hydroxy group resulting from the broken lactone ring and this, of course, adds an extra step to the reaction sequence.

In addition to the preparation of a carboxylate ester by solvolysis as described above, these esters may also be prepared by reacting the lactone of formula (I) or the carboxylic acid of formula (II) with a diazo compound, preferably diazomethane or a C-substituted diazomethane, under the reaction conditions described in United Kingdom Patent Specification No. 1,555,831.

Amino acid carboxylate salts of the compounds of formula (II), that is to say compounds of formula (VIII) in which A represents an amino acid, may be prepared from any of the compounds of formulae (V), (X), (VI), (III) and (II), preferably the compounds of formulae (III), (VI) or (II), by the methods described in United Kingdom Patent Specification No. 1,555,831.

Amine salts of the compounds of formula (II), that is to say compounds of formula (VIII) in which A represents an organic amine or ammonia, may be prepared from any of the compounds of formulae (V), (X), (VI) and (III) by first preparing the corresponding alkali metal carboxylate salt, by the hydrolysis reaction described above, for example the sodium carboxylate, and then reacting this with a mineral acid (e.g. hydrochloric acid) salt of ammonia or of an organic amine in a suitable solvent. The nature of the solvent is not critical, provided that it has no adverse effect upon the reaction, aqueous solvents being preferred. Examples include water itself and mixtures of water with one or more organic solvents, such as alcohols (e.g. methanol or ethanol) or ketones (e.g. acetone). The amount of amine salt is preferably equimolar or a slight molar excess, with respect to the metal carboxylate, e.g. a molar ratio amine salt: metal carboxylate of from 1:1 to 1.2:1. The reaction is preferably effected at a pH value of from 7.0 to 8.5 and a temperature of ambient or below, e.g. from 0° C. to 10° C., more preferably from 5° C. to 10° C. After the reaction, the resulting salt may be separated from the reaction mixture by extraction with a suitable solvent, such as ethyl acetate.

Where the compound of the invention has one or two hydroxyimino groups, it may be converted to a hydroxyimino salt. The starting material for this reaction can be the compound of formula (II) or a salt or ester thereof or it can be the corresponding lactone, i.e. the compound of formula (VI). It is also possible to use as the starting material the lactones of formula (X) or their corresponding free hydroxycarboxylic acids or salts. In general, the product will be the hydroxyimino salt of the carboxylate salt or carboxylate ester; preparation of a hydroxyimino salt of the carboxylic acid or of the lactone is difficult.

The reaction is preferably effected by contacting the appropriate starting material with a metal hydroxide in a suitable solvent. Examples of metal hydroxides which may be employed in this reaction include alkali metal hydroxides (e.g. sodium hydroxide or potassium hydroxide) and alkaline earth metal hydroxides (e.g. calcium hydroxide or barium hydroxide), preferably alkali metal hydroxides. Where the starting material is a salt or ester, e.g. a salt or ester of the compound of formula (II), the amount of metal hydroxide employed is preferably from 0.9 to 1.1 equivalents per equivalent of hydroxyimino group in the starting material; on the other hand, where the starting material is a lactone, i.e. the compound of formula (X) or (VI), the amount of metal hydroxide preferably employed is from 0.9 to 1.1 equivalents per equivalent of hydroxyimino group plus an extra amount of from 1 to 1.5 equivalents. Accordingly, where the starting material is a lactone, the amount of metal hydroxide is from 1.9 to 2.6 equivalents per mole of lactone if the lactone contains a single hydroxyimino group or from 2.8 to 3.7 equivalents per mole of lactone if the lactone contains two hydroxyimino groups.

The reaction is preferably effected at about ambient temperature and the time allowed for the reaction is preferably from 1 to 3 hours.

After completion of the reaction, the desired compound may be recovered from the reaction mixture by conventional means. For example, the solvent may be removed from the reaction mixture by distillation under reduced pressure, after which the resulting residue is freeze-dried, to give the desired compound. This compound may, if required, be further purified by conventional means, for example by recrystallisation or the various chromatographic techniques, especially column chromatography.

The compounds of the invention in which one or both of the groups represented by $R^1$ and $R^2$ is a group of formula $=N-OR^3$ have been found to inhibit cholesterol biosynthesis in the same may as do the known ML-236A, ML-236B, MB-530A and MB-530B, but have a significantly more potent activity. The compounds of the invention in which $R^1$ and $R^2$ both represent oxygen atoms are, as already described, valuable intermediates for the synthesis of the active compounds. The inhibitory activities of certain of the compounds of the invention, in terms of the concentration in ng/ml required to inhibit cholesterol biosynthesis by 50% [measured by the method described in the Journal of Biological Chemistry, 234, 2835 (1959)], are as follows (for comparison, the value for ML-236B lactone is also given):

| | |
|---|---|
| 3,4-dihydro-6-oxo-4-hydroxyiminoIsoML-236A lactone | 0.9 |
| 3,4-dihydro-6-oxo-4-hydroxyiminoIsoML-236B lactone | 0.3 |
| 3,4-dihydro-6-oxo-4-methoxyiminoIsoML-236B lactone | 0.6 |

| | |
|---|---|
| sodium 3,4-dihydro-6-oxo-4-hydroxyiminoIsoML-236B carboxylate | 0.3 |
| disodium 3,4-dihydro-6-oxo-4-oxidoiminoIsoML-236B carboxylate | 0.4 |
| 3,4-dihydro-4,6-bis(hydroxyimino)IsoML-236B lactone | |
| isomer a (Example 3) | 4.5 |
| isomer b (Example 3) | 4.3 |
| ML-236B lactone | 10 |

The compounds of the invention can, therefore, be used for purposes where it is desirable to inhibit the biosynthesis of cholesterol, for example as antihyperlipaemic agents or antiarteriosclerosis agents. The compounds of the invention may be administered by any conventional means, for example parenterally (e.g. by subcutaneous, intravenous or intramuscular injection) or orally (e.g. in the form of tablets, capsules, powders or granules). The adult daily dose will, of course, vary, depending upon the age, body weight and condition of the patient, as well as upon the route and times of administration, but, in general, the compounds of the invention are preferably administered in an amount of from 0.5 to 500 mg per day, in a single dose or in divided doses, e.g. 3 or 4 doses daily. However, if desired, larger doses may be administered.

The preparation of the compounds of the invention is further illustrated by the following Examples.

EXAMPLE 1

3,4-Dihydro-6-oxo-4-hydroxyiminoIsoML-236B lactone (i)
16-t-Butyldimethylsilyloxy-3,4-dihydro-4,6-dioxoIsoML-236B lactone 2.0 g of ML-236B lactone were dissolved in 20 ml of dimethylformamide. To the resulting solution were added 418 mg of imidazole and 850 mg of t-butyldimethylsilyl chloride, after which the mixture was stirred at 40°–45° C. for 3.5 hours. At the end of this time, the reaction mixture was diluted with 100 ml of ethyl acetate, washed twice with water and then dried over Glauber's salt. The solvent was distilled off under reduced pressure, and the residue was purified by column chromatography through silica gel, eluted with a mixture of hexane and ethyl acetate in proportions ranging from 8 : 2 to 1 : 1 by volume, to give fractions containing 2.1 g of 16-t-butyldimethylsilyloxyML-236B lactone, mass spectrum (m/e): 504 (M+).

10.1 g of this compound were then added to a Collins' reagent prepared from 22.3 g of pyridine, 14.3 g of chromic anhydride and 300 ml of methylene chloride, with ice-cooling. The mixture was then stirred at room temperature overnight, after which it was diluted with about 200 ml of ethyl acetate and the mixture was filtered using a Celite (trade mark) filter aid. The filtrate was concentrated by evaporation under reduced pressure and the residue was purified by column chromatography through silica gel, eluted with a mixture of hexane and ethyl acetate in proportion ranging from 8:2 to 1:1 by volume, to give fractions containing 4.3 g of the desired compound.

Infrared absorption spectrum (liquid film) $\nu_{max}$cm$^{-1}$: 1735, 1700, 1680.

Nuclear Magnetic Resonance spectrum (at 90 MHz, CDCl$_3$) δppm: 0.88 (9H, singlet, t-butyl); 1.03 (3H, doublet, J=7.0 Hz, 11-CH$_3$); 1.10 (3H, doublet, J=7.0 Hz, 2- CH$_3$ of 2-methylbutyryl); 2.57 (2H, doublet, J=4.0 Hz, CH$_2$ at 17-position); 4.28 (1H, multiplet, CH at 16-position); 4.40–4.76 (1H, multiplet, CH at 14-position); 5.51 (1H, broad singlet, CH at 1-position); 6.57 (1H, doublet, J=2.0 Hz, CH at 5-position).

Mass Spectrum (m/e): 534 (M+), 432 (M -102).

(ii)
16-t-Butyldimethylsilyloxy-3,4-dihydro-6-oxo-4-hydroxyiminoIsoML-236B lactone and 16-t-butyldimethylsilyloxy-3,4-dihydro-4oxo-6-hydroxyiminoIsoML-236B lactone To a solution of 500 mg (0.935 mmole) of the compound obtained in step (i) above in 10 ml of dioxane and 0.5 ml of water were added 84.7 mg (1.03 mmole) of sodium acetate and 71.5 mg (1.03 mmole) of hydroxylamine hydrochloride, with ice-cooling. The mixture was then stirred at room temperature for 1.5 hours, after which it was diluted with about 20 ml of ethyl acetate, washed with water and dried over Glauber's salt. The solvent was then distilled off under reduced pressure and the residue was purified by chromatography through a Lobar column filled with silica gel and eluted with a 3:2 by volume mixture of chloroform and ethyl acetate, to afford 245 mg of the desired 6-oxo-4-hydroxyimino compound and 73 mg of the desired 4-oxo-6-hydroxyimino compound.

6-Oxo-4-hydroxyimino compound
Infrared absorption spectrum (Nujol-trade markmull) $\nu_{max}$cm$^{-1}$: 3225, 1735, 1640.
Mass Spectrum (m/e): 549 (M+).
4-Oxo-6-hydroxyimino compound:
Mass Spectrum (m/e): 549 (M+).

(iii) 3,4-Dihydro-6-oxo-4-hydroxyiminoIsoML-236B lactone 245 mg of 16-t-butyldimethylsilyloxy-3,4-dihydro-6-oxo-4-hydroxyiminoIsoML-236B lactone, prepared as described in step (ii) above, were dissolved in 5 ml of tetrahydrofuran. To the resulting solution were added 0.2 ml of acetic acid and 600 mg of tetrabutylammonium fluoride, after which the mixture was stirred at room temperature for 48 hours. The mixture was then diluted with about 10 ml of ethyl acetate, washed with water and dried over Glauber's salt. The solvent was distilled off under reduced pressure, and the resulting residue was purified by column chromatography through silica gel, eluted with a 95:5 by volume mixture of chloroform and methanol, to give 151 mg of the title compound.

Infrared absorption spectrum (Nujol mull) $\nu_{max}$cm$^{-1}$: 3300, 1730, 1650.

Nuclear Magnetic Resonance spectrum (at 90 MHz, deuteroacetone) δppm: 0.87 (3H, triplet, J=7.0 Hz, 4-CH$_3$ of 2-methylbutyryl); 1.00 (3H, doublet, J=7.0 Hz, 11-CH$_3$); 1.08 (3H, doublet, J=7.0 Hz, 2-CH$_3$ of 2-methylbutyryl); 2.75 (1H, singlet, 16-OH); 4.18–4.44 (1H, multiplet, CH at 16-position); 4.44–4.80 (1H, multiplet, CH at 14-position); 5.51 (1H, broad singlet, CH at 1-position); 6.44 (1H, doublet, J=3.0 Hz, CH at 5-position); 10.82 (1H, singlet, =N-OH).

Mass Spectrum (m/e): 435 (M+), 417 (M-18).

EXAMPLE 2

3,4-Dihydro-4-oxo-6-hydroxyiminoIsoML-236B lactone

The procedure described in Example 1 (iii) was repeated, except that 73 mg of 16-t-butyldimethylsilyloxy-3,4-dihydro-4-oxo-6-hydroxyiminoIsoML-236B lactone, prepared as described in Example 1 (ii), were used in place of the 6-oxo-4-hydroxyimino compound, to give 24 mg of the title compound.

Infrared absorption spectrum (Nujol mull) $\nu_{max}$cm$^{-1}$: 3350, 1725, 1700, 1685, 1600.

Nuclear Magnetic Resonance spectrum (at 90 MHz, deuteroacetone) δppm: 0.88 (3H, triplet, J=7.0 Hz, 4-CH$_3$ of 2-methylbutyryl); 0.96 (3H, doublet, J=7.0 Hz, 11-CH$_3$); 1.10 (3H, doublet, J=7.0 Hz, 2-CH$_3$ of 2-methylbutyryl); 2.75 (1H, singlet, 16-OH); 4.18–4.48 (1H, multiplet, CH at 16-position): 4.48–4.80 (1H, multiplet, CH at 14-position); 5.47 (1H, multiplet, CH at 1-position): 6.92 (1H, doublet, J=3.0 Hz, CH at 5-position); 10.67 (1H, singlet, =N-OH).

Mass spectrum (m/e): 435 (M+), 417 (M-18).

EXAMPLE 3

3,4-Dihydro-4,6-bis(hydroxyimino)IsoML-236B lactone

A hydroxylamine solution prepared from 175 mg (25 mmole) of sodium acetate, 173 mg (25 mmole) of hydroxylamine hydrochloride and 2.5 ml of dioxane was added dropwise, with ice-cooling and stirring, to a solution of 573 mg of the diketone compound prepared as described in Example 1 (i) in 10 ml of dioxane. The mixture was then stirred, with ice-cooling, for a further 1.5 hours. At the end of this time, the reaction mixture was diluted with 30 ml of ethyl acetate, washed with water and dried over Glauber's salt. The solvent was distilled off under reduced pressure and the residue was purified by column chromatography through silica gel eluted with a mixture of chloroform and acetone in proportions ranging from 10:0 to 7:3.

The resulting fractions contained the desired 16-t-butyldimethylsilyloxy-3,4-dihydro-4,6-bis(hydroxyimino)IsoML-236B lactone in the form of two diastereoisomers, owing to the syn- and anti-configuration of the two hydroxyimino groups; the diastereoisomers were isolated separately, giving 255 mg of isomer a and 78 mg of isomer b.

Isomer a

Rf value: 0.22 [on silica gel, developed with a 1:1 by volume mixture of hexane and ethyl acetate (twice developed)].

Isomer b

Rf value: 0.12 [on silica gel, developed with a 1:1 by volume mixture of hexane and ethyl acetate (twice developed)].

The two isomers were separately desilylated.

First, following the procedure described in Example 1 (iii), 230 mg of isomer a were treated with 2.3 ml of acetic acid, 503 mg of tetrabutylammonium fluoride and 10 ml of tetrahydrofuran, to give 101 mg of isomer a of the title compound.

Infrared absorption spectrum (Nujol mull) $\nu_{max}$cm$^{-1}$: 3300, 1720.

Nuclear Magnetic Resonance spectrum (at 90 MHz, deuteroacetone) δppm: 0.87 (3H, triplet, J=7.0 Hz, 4-CH$_3$ of 2-methylbutyryl): 0.96 (3H, doublet, J=7.0 Hz, 11-CH$_3$); 1.09 (3H, doublet, J=7.0 Hz, 2-CH$_3$ of 2-methylbutyryl); 2.80 (1H, broad singlet, 16-OH); 4.18–4.47 (1H, multiplet, CH at 16-position); 4.47–4.82 (1H, multiplet, CH at 14-position); 5.41 (1H, broad singlet, CH at 1-position); 6.74 (1H, doublet, J=3.0 Hz, CH at 5-position); 10.05 (1H, broad singlet,=N-OH); 10.30 (1H, broad singlet,=N-OH);

Mass spectrum (m/e): 450 (M+), 432 (M-18).

Following the procedure described in Example 1 (iii), 60 mg of isomer b were treated width 0.06 ml of acetic acid, 131 mg of tetrabutylammonium fluoride and 3 ml of tetrahydrofuran, to give 37 mg of isomer b of the title compound.

Infrared absorption spectrum (Nujol mull) $\nu_{max}$cm$^{-1}$: 3325, 1720.

Nuclear Magnetic Resonance spectrum (at 90 MHz, deuteroacetone) δppm: 0.87 (3H, triplet, J=7.0 Hz, 4-CH$_3$ of 2-methylbutyryl); 0.96 (3H, doublet, J=7.0 Hz, 11-CH3); 1.09 (3H, doublet, J=7.0 Hz, 2-CH$_3$of 2-methylbutyryl); 4.10–4.46 (1H, multiplet, CH at 16-position); 4.46–4.81 (1H, multiplet, CH at 14-position); 5.43 (1H, broad singlet, CH at 1-position); 7.30 (1H, doublet, J=3.0 Hz, CH at 5-position); 9.7–10.56 (2H, broad singlet, two =N-OH groups);

EXAMPLE 4

Sodium 3,4-dihydro-6-oxo-4-hydroxyiminoIsoML-236B carboxylate

1 Equivalent of a 0.1N aqueous solution of sodium hydroxide was added, with stirring, at room temperature to 10 mg of 3,4-dihydro-6-oxo-4-hydroxyiminoIsoML-236B lactone, prepared as described in Example 1 (iii), after which the mixture was stirred for an additional 3 hours. The mixture was then freeze-dried, to give 10.3 mg of the title compound.

Mass spectrum (m/e): 475 (M+).

EXAMPLE 5

Disodium 3,4-dihydro-6-oxo-4-oxidoiminoIsoML-236B carboxylate

2 Equivalents of a 0.1N aqueous solution of sodium hydroxide were added, with stirring, at room temperature to 10 mg of 3,4-dihydro-6-oxo-4-hydroxyiminoIsoML-236B lactone, prepared as described in Example 1 (iii), after which the mixture was stirred for a further 3 hours. The mixture was then freeze-dried, to give 10.5 mg of the title compound.

Mass spectrum (m/e): 496 (M+).

EXAMPLE 6

3,4-Dihydro-6-oxo-4-methoxyiminoIsoML-236B lactone 423 mg of the diketone compound prepared as described in Example 1 (i) were dissolved in a mixture of 5 ml of dioxane and 0.3 ml of water. To the resulting solution were added, at room temperature, 41 mg of methoxyamine hydrochloride, after which the mixture was stirred at room temperature for 10 hours.

The reaction mixture was then diluted with 50 ml of ethyl acetate and 100 ml of benzene, after which it was washed with water and dried over Glauber's salt. The solvent was then distilled off under reduced pressure, to give a crude 16-t-butyldimethylsilyloxy-3,4-dihydro-6-oxo-4-methoxyiminoIsoML-236B lactone. The whole of this compound was dissolved in 5 ml of methylene chloride, and then 4 drops of trifluoroacetic acid were added to the solution. The resulting mixture was left to stand at room temperature for 10 hours, after which it was diluted with 50 ml of ethyl acetate and 50 ml of benzene; it was then washed with water and dried over Glauber's salt. The solvent was then distilled off under reduced pressure and the residue was purified by chromatography through a Lobar column containing silica gel, eluted with a 5 : 1 by volume mixture of chloroform and methanol, to give 112 mg of the title compound.

Nuclear Magnetic Resonance spectrum (at 90 MHz, deuteroacetone) δppm: 2.62 (2H, doublet, $CH_2$ at 17-position); 3.90 (3H, singlet, methoxy of methoxyimino); 4.31 (1H, multiplet, CH at 16-position); 4.65 (1H, multiplet, CH at 14-position); 5.50 (1H, broad singlet, CH at 1-position); 6.50 (1H, doublet, J=3.0 Hz, CH at 5-position).

Mass spectrum (m/e): 449 (M+), 431 (M-18).

EXAMPLE 7

(i) 1,16-Bis(t-butyldimethylsilyloxy)-3,4-dihydro-4,6-dioxoIsoML236A lactone 2.0 g of ML-236A lactone were dissolved in 20 ml of dimethylformamide; to the resulting solution were added 830 mg of imidazole and 1.7 g of t-butyldimethylsilyl chloride, after which the mixture was stirred at 40°-45° C. for 3.5 hours. The reaction mixture was then diluted with 100 ml of ethyl acetate, washed twice with water and dried over Glauber's salt. The solvent was distilled off under reduced pressure and the residue was purified by column chromatography through silica gel eluted with a mixture of hexane and ethyl acetate in proportions varying from 8:2 to 1:1, to give 2.3 g of 1,16-bis(t-butyldimethylsilyloxy)ML-236A lactone.

Infrared absorption spectrum (liquid film) $v_{max}cm^{-1}$: 1705.

Mass spectrum (m/e): 534 (M+).

5 g of 1,16-bis(t-butyldimethylsilyloxy)ML-236A lactone, prepared as described above, were added, with ice-cooling, to a Collins' reagent prepared from 11.2 g of pyridine, 7.2 g of chromic anhydride and 150 ml of methylene chloride, after which the mixture was stirred overnight at room temperature. The mixture was then diluted with about 100 ml of ethyl acetate and filtered using a Celite filter aid. The filtrate was concentrated by evaporation under reduced pressure and the residue was purified by column chromatography through silica gel eluted with a mixture of hexane and ethyl acetate in proportions varying from 8:2 to 1:1, to give fractions containing 3.2 g of the title compound.

Infrared absorption spectrum (liquid film) $v_{max}cm^{-1}$: 1735, 1700, 1680.

Mass spectrum (m/e): 564 (M+).

(ii) 3,4-Dihydro-6-oxo-4-hydroxyiminoIsoML-236A lactone 42 mg (0.52 mmole) of sodium acetate and 36 mg (0.52 mmole) of hydroxylamine hydrochloride were added, with ice-cooling, to a solution of 267 mg (0.5 mmole) of the compound prepared in step (i) above in 5 ml of dioxane and 0.3 ml of water. The mixture was then stirred at room temperature for 1.5 hours, after which it was diluted with about 10 ml of ethyl acetate, washed with water and dried over Glauber's salt. The solvent was then distilled off under reduced pressure and the residue was purified by chromatography through a Lobar column containing silica gel and eluted with a 3:2 by volume mixture of chloroform and ethyl acetate, to give 180 mg of 1,16-bis(t-butyldimethylsilyloxy)-3,4-dihydro-6-oxo-4-hydroxyiminoIsoML-236A lactone.

The whole of this compound was dissolved in 3 ml of tetrahydrofuran, and 0.15 ml of acetic acid and 400 mg of tetrabutylammonium fluoride were added to the resulting solution, after which the mixture was stirred at room temperature for 48 hours. The reaction mixture was then diluted with 5 ml of ethyl acetate, washed with water and dried over Glauber's salt. The solvent was distilled off under reduced pressure and the resulting residue was purified by column chromatography through silica gel eluted with a 95:5 by volume mixture of chloroform and methanol, to give 103 mg of the title compound.

Infrared absorption spectrum (Nujol mull) $v_{max}cm^{-1}$: 3200, 1710, 1640.

Nuclear Magnetic Resonance spectrum (at 90 MHz, deuteroacetone) δppm: 1.13 (3H, doublet, J=7.0 Hz, 11-$CH_3$); 4.02–4.43 (1H, multiplet, CH at 16-position); 4.43–4.80 (1H, multiplet, CH at 14-position); 6.23 (1H, broad singlet, CH at 1-position); 6.93 (1H, singlet, CH at 5-position); 11.07 (1H, broad singlet, =N-OH).

Mass spectrum (m/e): 317 (M+), 299

EXAMPLE 8

(i) 16-t-Butyldimethylsilyloxy-3,4-dihydro-4,6-dioxoIsoMB-530B lactone 8.0 g of MB-530B lactone were dissolved in 50 ml of dimethylformamide, and 1.63 g of imidazole and 3.62 g of t-butyldimethylsilyl chloride were added to the resulting solution, which was then stirred at 40°-45° C. for 3 hours. The mixture was then diluted with 300 ml of ethyl acetate, washed three times with water and then dried over Glauber's salt. The solvent was distilled off under reduced pressure and the residue was purified by column chromatography through silica gel eluted with a mixture of hexane and ethyl acetate in proportions varying from 8:2 to 1:1, to give 7.7 g of 16-t-butyldimethylsilyloxyMB-530B.

Mass spectrum (m/e): 518 (M+).

A solution of 7.5 g of this compound in 50 ml of methylene chloride was added dropwise, with ice-cooling, to a Collins'reagent prepared from 16.1 g of pyridine, 10.3 g of chromic anhydride and 200 ml of methylene chloride, after which the mixture was stirred overnight at room temperature. The mixture was then diluted with about 300 ml of ethyl acetate, stirred and filtered using a Celite filter aid. The filtrate was concentrated by evaporation under reduced pressure and the residue was purified by column chromatography through silica gel eluted with a mixture of hexane and ethyl acetate in proportions varying from 8:2 to 1:1 by volume, to afford 3.1 g of the title compound., Infrared absorption spectrum (liquid film) $v_{max}cm^{-1}$: 1735, 1700, 1680.

Nuclear Magnetic Resonance spectrum ($CDCl_3$) δppm: 0.88 (9H, singlet, t-butyl); 1.03 (3H, doublet, J=7.0 Hz, 11-$CH_3$); 1.10 (3H, doublet, J=7.0 Hz, 2-$CH_3$ of 2-methylbutyryl); 1.15 (3H, doublet, J=7.0 Hz, CH₃ substituent at 3-position); 4.28 (1H, multiplet, CH at 16-position); 4.40–4.80 (1H, multiplet, CH at 14-position); 5.51 (1H, broad singlet CH at 1-position); 6.60 (1H, doublet, J=3.0 Hz, CH at 5-position).

Mass spectrum (m/e): 548 (M+), 446 (M-102).

(ii) Oximation of 16-t-butyldimethylsilyloxy-3,4-dihydro-4,6-dioxoIsoMB-530B lactone A hydroxylamine solution prepared from 890 mg of sodium acetate, 760 mg of hydroxylamine hydrochloride, 12.5 ml of dioxane and 12.5 ml of water was added dropwise, with ice-cooling, to a solution of 3.0 g of 16-t-butyldimethylsilyloxy-3,4-dihydro-4,6-dioxoIsoMB-530B lactone, prepared as described in step (i) above, in 25 ml of dioxane; the mixture was then stirred for 1.5 hours. At the end of this time, the mixture was diluted with 300 ml of ethyl acetate, washed with water and dried over Glauber's salt. The solvent was distilled off under reduced pressure and the residue was purified through a Lobar column (a product of Merck & Co. Inc, Si-60, size B x 2), eluted with mixtures of hexane and ethyl acetate in proportions ranging from 3 : 7 to 6 : 4, to give four fractions containing desired compounds: 155 mg of fraction 1; 168 mg of fraction 2; 183 mg of fraction 3; and 375 mg of fraction 4.

(iii) 3,4-Dihydro-4-oxo-6-hydroxyiminoIsoMB-530 lactone

The procedure described in Example 1 (iii) was repeated, but using 127 mg of fraction 1, obtained as described in step (ii) above, 0.mole of acetic acd and 300 mg of tetrabutylammonium fluoride, to give 64 mg of the title compound.

Infrared absorption spectrum (Nujol mull) $\nu_{max}$ cm$^{-1}$: 3350, 1730, 1700.

Nuclear Magnetic Resonance spectrum (deuteroacetone) δppm: 0.88 (3H, triplet, J=7.0, 4-CH₃ of 2-methylbutyryl); 0.95 (3H, doublet, J=7.0 Hz, 11-CH₃); 1.09 (3H, doublet, J=7.0 Hz, 2-CH₃ of 2-methylbutyryl); 1.16 (3H, doublet, J=7.0 Hz, methyl substituent at 3-position); 4.18–4.43 (1H, multiplet, CH at 16-position); 4.43–4.78 (1H, multiplet, CH at 14-position); 5.48 (1H, broad singlet, CH at 1-position); 6.90 (1H, doublet, J=3.0 Hz, CH at 5-position); 10.52 (1H, singlet, =N-OH).

Mass spectrum (m/e): 449 (M+).

(iv) 3,4-Dihydro-6-oxo-4-hydroxyiminoIoMB-530B lactone

The procedure described in Example 1 (iii) was repeated, but using 127 mg of fraction 2, prepared as described in step (ii) above, 0.1 ml of acetic acid and 300 mg of tetrabutylammonium fluoride, to give 46 mg of the title compound.

Infrared absorption spectrum (Nujol mull) $\nu_{max}$ cm$^{-1}$: 3300, 1730, 1650.

Nuclear Magnetic Resonance spectrum (deuteroacetone) δppm: 0.87 (3H, triplet, J=7.0 Hz, 4-CH₃ of 2-methylbutyryl); 1.03 (3H, doublet, J=7.0 Hz, 11-CH₃); 1.10 (3H, doublet, J=7.0 Hz, 2-CH₃ of 2-methylbutyryl); 1.11 (3H, doublet, J=7.0 Hz, methyl substituent at 3-position); 4.20–4.40 (1H, multiplet, CH at 16-position); 4.40–4.80 (1H, multiplet, CH at 14-position); 5.50 (1H, broad singlet, CH at 1-position); 6.43 (1H, doublet, J=3.0 Hz, CH at 5-position); 10.70 (1H, singlet, =N-OH).

Mass spectrum (m/e): 449 (M+).

(v) 3,4-Dihydro-4,6-bis(hydroxyimino)IsoMB-530B lactone, isomer a

The procedure described in Example 1 (iii) was repeated, but using 118 mg of fraction 3, prepared as described in step (ii) above, 1.15 ml of acetic acid and 252 mg of tetrabutylammonium fluoride, to give 57 mg of the desired isomer a.

Infrared absorption spectrum (Nujol mull) $\nu$ maxcm$^{-1}$: 3300, 1725.

Nuclear Magnetic Resonance spectrum (deuteroacetone) δppm:

0.87 (3H, doublet, J=7.0 Hz, 4-CH₃ of 2-methylbutyryl); 0.96 (3H, doublet, J=7.0 Hz, 11-CH₃); 1.09 (3H, doublet, J=7.0 Hz, 2-CH₃ of 2-methylbutyryl); 1.13 (3H, doublet, J=7.0 Hz, methyl substituent at 3-position); 4 17–4.44 (1H, multiplet, CH at 16-position); 4.44–4.80 (1H, multiplet, CH at 14-position); 5.40 (1H, broad singlet, CH at 1-position); 6.70 (1H, doublet, J=3.0 Hz, CH at 5-position); 10.10 (1H, broad singlet, =N-OH); 10.28 (1H, broad singlet, =N-OH).

Mass spectrum (m/e): 464 (M+).

(vi) 3,4-Dihydro-4,6-bis(hydroxyimino)IsoMB-530B lactone, isomer b

The procedure described in Example 1 ( iii) was repeated, except that 118 mg of fraction 4, prepared as described in step (ii) above, 1.15 ml of acetic acid and 252 mg of tetrabutylammonium fluoride were used, to give 38 mg of the desired isomer b.

Infrared absorption spectrum (Nujol mull) $\nu_{max}$ cm$^{-1}$: 3325, 1720.

Nuclear Magnetic Resonance spectrum (deuteroacetone) δppm: 0.87 (3H, triplet, J=7.0 Hz, 4-CH₃ of 2-methylbutyryl); 0.96 (3H, doublet, J=7.0 Hz, 11-CH₃); 1.10 (3H, doublet, J=7.0 Hz, 2-CH₃ of 2-methylbutyryl); 1.11 (3H, doublet, J=7.0 Hz, methyl substituent at 3-position); 4.11–4.46 (1H, multiplet, CH at 16-position); 4.46–4.80 (1H, multiplet, CH at 14-position); 5.43 (1H, broad singlet, CH at 1-position); 7.30 (1H, doublet, J=3.0 Hz, CH at 5-position); 10.00 (1H, broad singlet, =N-OH); 10.37 (1H, broad singlet, =N-OH).

Mass spectrum (m/e): 464 (M+).

EXAMPLE 9

Sodium 3,4-dihydro-6-oxo-4-hydroxyiminoIsoMB-530B carboxylate 0.23 ml of a 0.1N aqueous solution of sodium hydroxide was added to 10 mg of 3,4-dihydro-6-oxo-4-hydroxyiminoIsoMB-530B lactone. The mixture was stirred at room temperature for 3 hours and then freeze-dried to give 10.4 mg of the title compound.

Mass spectrum (m/e): 489 (M+).

We claim:

1. The compounds of the formula:

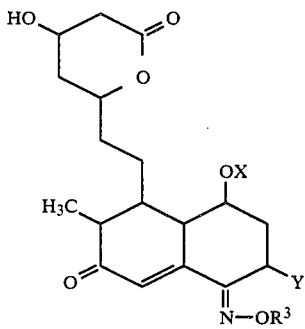

wherein:
X is a hydrogen atom or a 2-methylbutyryl group;
Y is a hydrogen atom or a methyl group; and
$R^3$ is a hydrogen atom or an alkyl group having 1-6 carbon atoms.

2. The compounds of claim 1 wherein Y is hydrogen.
3. The compounds of claim 1 wherein Y is methyl group.
4. The compounds of claim 2 wherein X is hydrogen.
5. The compounds of claim 2 wherein X is a 2-methylbutyryl group.
6. The compounds of claim 3 wherein X is hydrogen.
7. The compounds of claim 3 wherein X is a 2-methylbutyryl group.
8. The compounds of claim 2 wherein $R^3$ is hydrogen.
9. The compounds of claim 3 wherein $R^3$ is hydrogen.
10. The compounds of claim 4 wherein $R^3$ is hydrogen.
11. The compounds of claim 5 wherein $R^3$ is hydrogen.
12. The compounds of claim 6 wherein $R^3$ is hydrogen.
13. The compounds of claim 7 wherein $R^3$ is hydrogen.
14. The compounds of claim 2 wherein $R^3$ is a lower alkyl group having 1-6 carbon atoms.
15. The compounds of claim 3 wherein $R^3$ is a lower alkyl group having 1-4 carbon atoms.
16. The compounds of claim 4 wherein $R^3$ is a lower alkyl group having 1-4 carbon atoms.
17. The compounds of claim 5 wherein $R^3$ is a lower alkyl group having 1-4 carbon atoms.
18. The compounds of claim 6 wherein $R^3$ is a lower alkyl group having 1-4 carbon atoms.
19. The compounds of claim 7 wherein $R^3$ is a lower alkyl group having 1-4 carbon atoms.
20. The compounds of claim 2 wherin $R^3$ is a methyl group.
21. The compounds of claim 3 wherein $R^3$ is a methyl group.
22. The compounds of claim 4 wherein $R^3$ is a methyl group.
23. The compounds of claim 5 wherein $R^3$ is a methyl group.
24. The compounds of claim 6 wherein $R^3$ is a methyl group.
25. The compounds of claim 7 wherein $R^3$ is a methyl group.
26. The compounds of claim 2 wherein $R^3$ is an ethyl group.
27. The compounds of claim 3 wherein $R^3$ is an ethyl group.
28. The compounds of claim 4 wherein $R^3$ is an ethyl group.
29. The compounds of claim 5 wherein $R^3$ is an ethyl group.
30. The compounds of claim 6 wherein $R^3$ is an ethyl group.
31. The compounds of claim 7 wherein $R^3$ is an ethyl group.

* * * * *